(12) United States Patent
Lui et al.

(10) Patent No.: US 8,093,421 B2
(45) Date of Patent: Jan. 10, 2012

(54) STEREOSELECTIVE ONE STEP FLUORINATION PROCESS FOR THE PREPARATION OF 2-FLOUROPROPIONATE

(75) Inventors: Norbert Lui, Odenthal (DE); Sergii Pazenok, Solingen (DE)

(73) Assignee: Bayer Cropscience AG, Monheim (DE)

( * ) Notice: Subject to any disclaimer, the term of this patent is extended or adjusted under 35 U.S.C. 154(b) by 81 days.

(21) Appl. No.: 12/446,774

(22) PCT Filed: Oct. 16, 2007

(86) PCT No.: PCT/EP2007/008944
§ 371 (c)(1),
(2), (4) Date: Apr. 23, 2009

(87) PCT Pub. No.: WO2008/049531
PCT Pub. Date: May 2, 2008

(65) Prior Publication Data
US 2010/0069663 A1    Mar. 18, 2010

(30) Foreign Application Priority Data
Oct. 27, 2006    (EP) .................................. 06022482

(51) Int. Cl.
*C07C 69/63*    (2006.01)
(52) U.S. Cl. ...................................................... 560/227
(58) Field of Classification Search .................. None
See application file for complete search history.

(56) References Cited

U.S. PATENT DOCUMENTS 5,723,654 A * 3/1998 Bertsch ...................... 560/227
7,462,734 B2 * 12/2008 Ishii et al. .................... 560/111

FOREIGN PATENT DOCUMENTS

EP    1 780 194    5/2007
WO    WO 2006/018991    * 2/2006

OTHER PUBLICATIONS

Petrov et al, Journal of Fluorine Chemistry, 1, 1, 2, 2-Tetrafluoroethyl-N, N-dimethylamine: A New Selective Fluorinating Agent, 2001, 109, pp. 25-31.*
Wantanabe et al, Journal of Fluorine Chemistry, Fluorination of Hydroxyesters With N, N- Diethyl-1,1, 2, 3, 3-Hexafluoropropylamine, 1986, 31, pp. 247-253.*
Hamman et al., J. Fluorine Chem., vol. 37, No. 1, Oct. 1987, pp. 85-94.

* cited by examiner

*Primary Examiner* — Paul A Zucker
(74) *Attorney, Agent, or Firm* — Frommer Lawrence & Haug LLP

(57) ABSTRACT

The current invention describes a one-step process for the synthesis of 2-fluoropropionates from lactic acid ester derivatives using TFEDMA.

10 Claims, No Drawings

STEREOSELECTIVE ONE STEP FLUORINATION PROCESS FOR THE PREPARATION OF 2-FLOUROPROPIONATE

The current invention describes a new process for the stereoselective synthesis of chiral 2-fluoropropionates.

Chiral 2-fluoropropionates are important intermediates for the preparation of herbicides (WO 01/068616, EP 1484324). There are several methods for the production of these optically active compounds described in the literature. DE-A 4131242, EP 1 671 939 and Tetrahedron: Asymmetry 1994, 5(6), 981 describe the preparation of optically active 2-fluorocarboxylic acids by the reaction of optically active 2-hydroxycarboxylic acids O-sulphonate with potassium fluoride using an amide as solvent. Chiral 2-(sulfonyloxy)carboxylate esters were prepared from hydroxyacids with methanesulphonylchloride in the presence of triethylamine (NEt$_3$) and dimethylaminopyridine (DMAP). This two step process produces a lot of waste and gives only moderate yield of the desired compound.

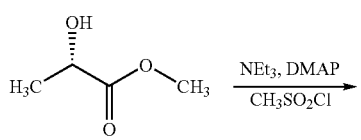

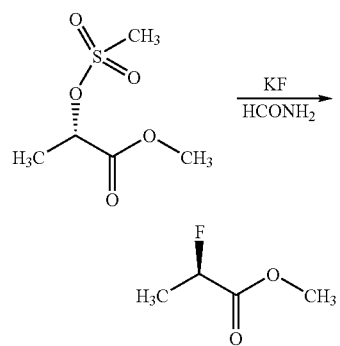

Another method for the preparation comprises thermal decomposition of fluorosulfites in the presence of amines (FR-A 2876100). This two/three step method utilizes dangerous reagents like HF and gives only moderate yield of the fluoropropionate.

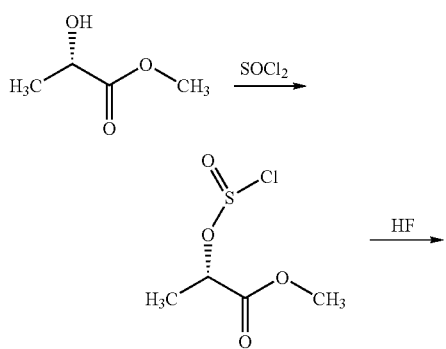

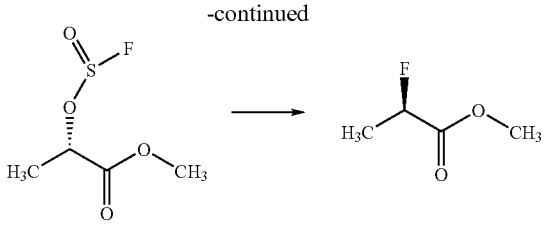

Hydroxy-groups in a hydoxypropionate can be directly replaced by fluorine using for instance diethylaminosulphurtrifluoride (DAST; Et$_2$N—SF$_3$) or Deoxofluor, but these reagents are very expensive and can not be used on a large scale due to their hazardous decomposition potential.

It is known that FAR reagents (Fluoroalkylamino reagents) like Yarovenko or Ishikawa reagent are able to replace hydroxy groups by fluorine in alcohols (*J. Obsch. Khim,* 1959, 29, 2159; *J. Fluor. Chem.* 2001, 109, 25). Usually fluorination of chiral alcohols is not enantioselective enough to be used for the commercial production of enantiomeric pure compounds.

R—CF$_2$—N(Et)$_2$

R═CF$_2$ or CFCl Yarovenko reagent

R═CF$_3$—CFH Ishikawa reagent

For instance fluorination of chiral pyrrolidines with FAR proceeds with inversion and only 75% ee (enantiomeric excess):

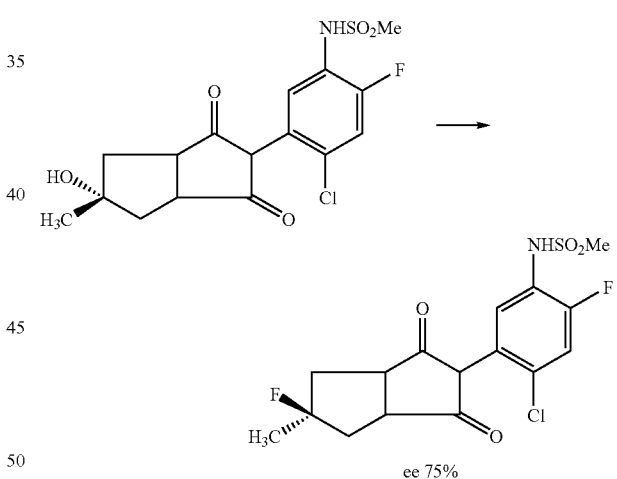

ee 75%

The utilisation of HCF$_2$—CF$_2$—NMe$_2$ (tetrafluoroethyldimethylamine or TFEDMA) for the fluorination of alcohols has been described by V. Petrov (*J. Fluor. Chem.* 2001, 109, p. 25; *Advance in organic Synthesis,* 2006, p. 269). There was no indication in the literature that the fluorination would occur with high enantioselectivity.

The fluorination of (R)-(−)-mandelic acid ester with Ishikawa reagent (1,1,2,3,3,3-hexafluoropropyldiethylamin) gave ethyl S-(+)-2-fluoro-2-pheny acetate with 76% ee J. Fluorine. Chemistry, 31(1986)247-253.

Moreover it has been mentioned (International Symposium on Fluorine Chemistry, Bremen 2006, Poster session, Org. 38, Petrov. et al.) that fluorination of many chiral compounds like (S)-(+)-mandelate with TFEDMA proceeds with low ee of 42-50%.

Surprisingly, it was now found that TFEDMA reacts with esters of lactic acid ester derivatives of formula (I) with inversion and very high ee (>95%) according to reaction scheme 1 to yield fluoropropionates of the formula (II):

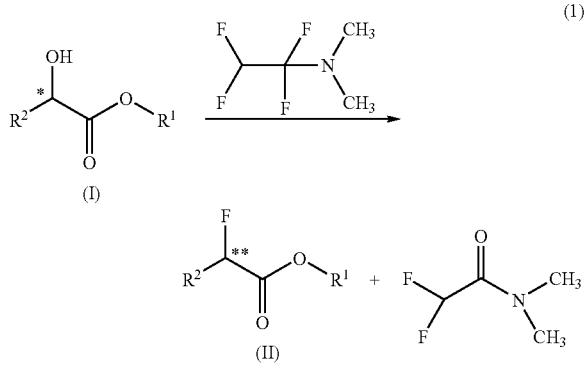

As educts are used lactic acid ester derivatives of the formula (I) wherein
* marks an asymmetric carbon atom in R- or S-configuration,
** marks an asymmetric carbon atom with inversed configuration in comparison to the above carbon atom marked *,
$R^1$ is optionally substituted $C_1$-$C_4$ alkyl and
$R^2$ is optionally substituted methyl.

The isolation of the desired product is very simple via distillation. It is worth to note that the major byproduct (dimethyl Amide of difluoroacetic acid) is commercially valuable.

Subject of the present invention is therefore a process for the enantioselective synthesis of chiral 2-fluoropropionates by the reaction of lactic acid ester derivatives with TFEDMA.

The process is generally described by reaction scheme 1. In the following, preferred embodiments are disclosed:

$R^1$ is preferably $C_1$-$C_4$ alkyl.

$R^2$ is preferably methyl optionally substituted by one more substituents independently selected from the group consisting of halogen, cyano, nitro, $C_1$-$C_4$-alkoxy, $C_1$-$C_4$-alkylthio, $C_1$-$C_4$-alkylsulphinyl, $C_1$-$C_4$-alkylsulphonyl, ($C_1$-$C_4$-alkoxy)carbonyl, $C_1$-$C_4$-alkylamino, di-($C_1$-$C_4$-alkyl)amino, $C_3$-$C_6$-cycloalkylamino oder ($C_1$-$C_4$-alkyl) $C_3$-$C_6$-cycloalkylamino.

$R^1$ is especially preferably methyl, ethyl, n-propyl or i-propyl.

$R^2$ is especially preferably methyl or ethyl both optionally substituted by one or more substituents selected independently from chlorine, bromine, iodine and fluorine.

$R^1$ is very especially preferably methyl or ethyl.

$R^2$ is very especially preferably methyl.

Thus, starting with methyl lactate as educt the process according to the invention can be represented by reaction scheme (2):

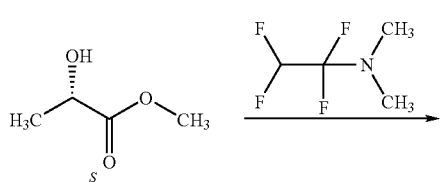

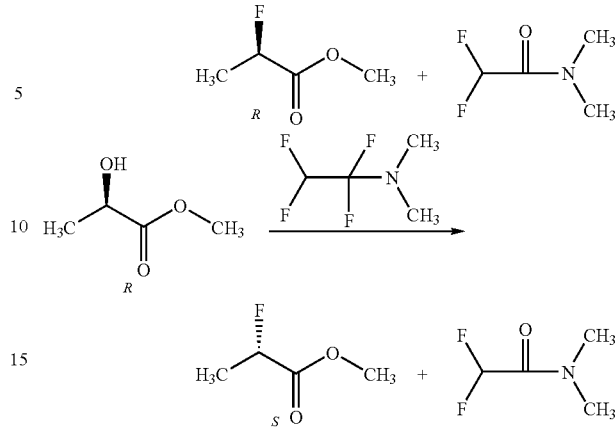

In this specific embodiment the process according to the invention takes place at room temperature without solvent or in the presence of a solvent like $CH_2Cl_2$ or $ClCH_2CH_2Cl$ within 8-20 h to give fluoropropionate in 70-85% yield and 96-97% ee (Reaction scheme 1).

The process according to the invention can be carried out in the presence of a suitable inert diluent. Most notably coming into consideration as diluents are: hydrocarbons such as, for example, pentane, hexane, heptane, octane, cyclohexane, methylcyclohexane, benzene, toluene, xylol, petrol ether, ligroin; halogenated hydrocarbons such as, for example, dichloromethane, trichloromethane, tetrachloromethane, 1,2-dichlorethane, chlorobenzene or dichlorobenzene; nitriles such as acetonitrile, propionitrile, butyronitrile; ethers such as, for example, diethyl ether, methyl ethyl ether, diisopropyl ether, dibutyl ether, dioxane, dimethoxyethane (DME), tetrahydrofuran diethylene glycol dimethyl ether (DGM); esters such as, for example, ethyl acetate, amyl acetate; acid amides such as, for example, dimethylformamide (DMF), dimethylacetamide (DMA), N-methylpyrrolidone, 1,3-dimethyl-2-imidazolidinone, hexamethylphosphoric acid triamide (HMPA). N-methylpyrrolidone, butyronitrile, dimethylacetamide (DMA), dioxane and 1,3-dimethyl-2-imidazolidinone are particularly preferred as diluents.

The process according to the invention can be carried out within a relatively large temperature range. The reaction is preferably carried out at temperatures between −10° C. and +80° C., in particular between 0° C. and 30° C. In order to keep the temperature in the suitable range, the mixing of both educts has to be done slowly, e.g. dropwise, and optionally under cooling.

The process according to the invention is generally carried out under standard pressure. However it is also possible to carry out the process according to the invention under increased or decreased pressure—in general between 0.1 bar and 50 bar, preferably between 1 bar and 10 bar.

For carrying out the process according to the invention, one generally adds between 0.75 mole and 3 moles, preferably between 0.8 mole and 2 moles of TFDMA to 1 mole of lactic acid ester derivative of the formula (I).

SYNTHETIC EXAMPLE 1

(R)-Methyl-2-fluoropropionate

To 10.4 g (0.1 mol) (S)-(−)-methyl lactate 21.75 g (0.15 mol) tertafluoroethyldimethylamine were slowly added dropwise to keep the temperature below 30° C. The reaction mixture was then stirred at room temperature for 12 hours. It was then poured on ice and the product extracted using dichloromethane. The product was further cleaned by distillation over a Vigreux distilling column. Three fractions were obtained.

Fraction 1 b.p. 45-50° C./15 mbar, 8.3 g (83%) R-methyl-2-fluoropropionate, 98% content and 96% ee (determined by Chirale GC). 98% Enantiomer R, 2% Enantiomer S.

$^1$H NMR: 1.5 (3H, dqw), 3.8 (3H, s), 5.1 (dqw, 1H) ppm.

Fraction 2 b.p. 60-65° C./15 mbar, 1 g lactic acid methyl ester (Educt).

Fraction 3 b.p. 70-80° C./15 mbar, 11.3 g difluoroacetic acid dimethylamide

SYNTHETIC EXAMPLE 2

(S)-Methyl-2-fluoropropinoate

Synthesis can be achieved according to example 1.

The invention claimed is:

1. Process for the production of a compound of the formula (II)

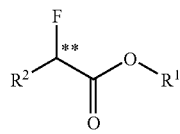

(II)

wherein
** marks an asymmetric carbon atom,
$R^1$ is optionally substituted $C_1$-$C_4$ alkyl and
$R^2$ is methyl which is optionally substituted by one or more substituents selected from the group consisting of halogen, cyano, nitro, $C_1$-$C_4$-alkoxy, $C_1$-$C_4$-alkylthio, $C_1$-$C_4$-alkylsulphinyl, $C_1$-$C_4$-alkylsulphonyl, ($C_1$-$C_4$-alkoxy)carbonyl, $C_1$-$C_4$-alkylamino, di-($C_1$-$C_4$-alkyl)amino, $C_3$-$C_6$-cycloalkylamino and ($C_1$-$C_4$-alkyl) $C_3$-$C_6$-cycloalkylamino, characterized in that tetrafluoroethyldimethylamine is reacted with a lactic acid derivative of the formula (I)

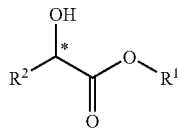

(I)

wherein
* marks an asymmetric carbon atom in R- or S-configuration and
$R^1$ and $R^2$ have the meaning given above,
the carbon atom marked ** in formula (II) having inversed configuration in comparison the corresponding carbon atom marked * in formula (I).

2. Process according to claim 1 characterized in that the reaction takes place in the presence of an inert diluent.

3. Process according to claim 1 characterized in that between 0.75 and 3 moles of tetrafluoroethyldimethylamine are reacted per mole of lactic acid derivative of formula (I).

4. Process according to claim 1, characterized in that $R^1$ and $R^2$ each represent methyl.

5. Process according to claim 1 characterized in that the compound of formula (II) is (R)-methyl-2-fluoroproprionate and the lactic acid derivative of the formula (I) is (S)-methyl lactate.

6. Process according to claim 1, characterized in that the compound of formula (II) is (S)-methyl-2-fluoroproprionate and the lactic acid derivative of the formula (I) is (R)-methyl lactate.

7. Process according to claim 1, wherein $R^1$ is methyl, ethyl, n-propyl or i-propyl.

8. Process according to claim 1, wherein $R^2$ is methyl or ethyl both optionally substituted by one or more substituents selected from the group consisting of chlorine, bromine, iodine and fluorine.

9. Process according to claim 1, wherein $R^1$ is methyl or ethyl.

10. Process according to claim 1, wherein the compound of formula (II) has an ee of >95% relative to its inverse configuration.

* * * * *